United States Patent [19]
Peter et al.

[11] Patent Number: 6,027,505
[45] Date of Patent: Feb. 22, 2000

[54] INSTRUMENT FOR THE INTRODUCTION OF AN INLAY OF AN IMPLANT INTO THE ASSOCIATED SHELL

[75] Inventors: Rolf Peter, Zürich; Thomas Willi, Winterthur; Burkhard Wymann, Elgg, all of Switzerland

[73] Assignee: Sulzer Orthopaedie AG, Baar, Switzerland

[21] Appl. No.: 09/110,100

[22] Filed: Jul. 2, 1998

[30] Foreign Application Priority Data

Jul. 4, 1997 [EP] European Pat. Off. ............. 97810445

[51] Int. Cl.⁷ ..................................................... A61F 5/04
[52] U.S. Cl. ................................................ 606/91; 606/99
[58] Field of Search ............................ 606/91, 99; 623/22

[56] References Cited

U.S. PATENT DOCUMENTS 5,098,437   3/1992   Kashuba .
5,540,697   7/1996   Rehmann .

FOREIGN PATENT DOCUMENTS

0453695A1   10/1991   European Pat. Off. .
2 676 172   11/1992   France .
2 299 758   10/1996   United Kingdom .
WO 94/21199  9/1994   WIPO .

*Primary Examiner*—Michael Buiz
*Assistant Examiner*—David D. Reip
*Attorney, Agent, or Firm*—Townsend and Townsend and Crew LLP

[57] ABSTRACT

An instrument (1) for the introduction of an inlay (E) of an implant, in particular of an artificial hip joint socket (HP), into the associated shell (S) of this implant, comprises a bar (2) which has a holder (5) at its distal end for holding the inlay (E) firmly. Furthermore, it comprises an actuating member (3, 30) for releasing the inlay (E) into the shell (S). The holder apparatus (5) comprises at least three resilient lamella (50) which point in the axial direction, are arranged in such a manner that their free ends point away from the bar (2) and are shaped in such a manner that they form a snap connection together with the inlay (E) when holding the inlay (E).

7 Claims, 2 Drawing Sheets

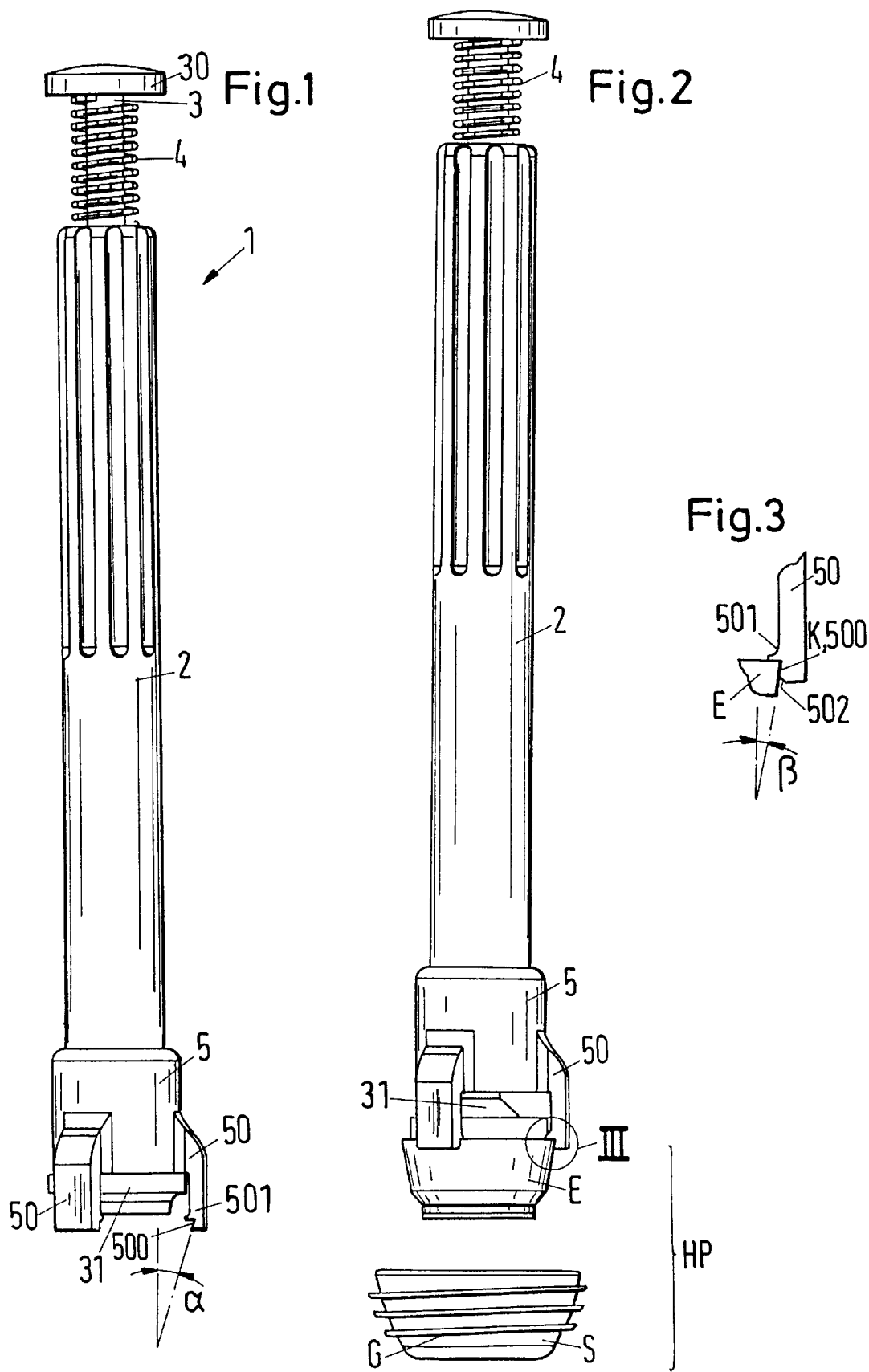

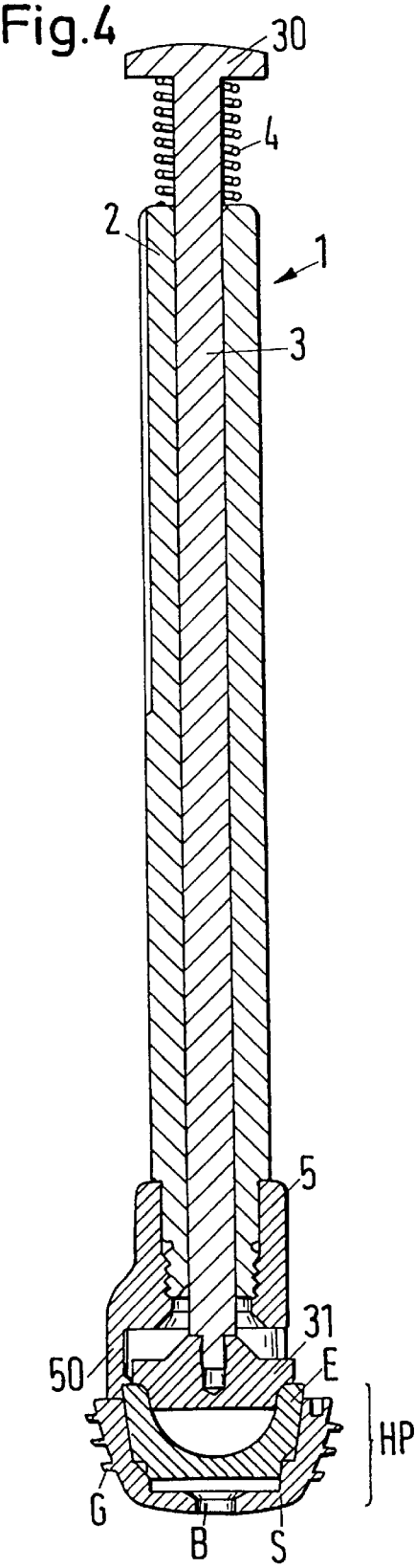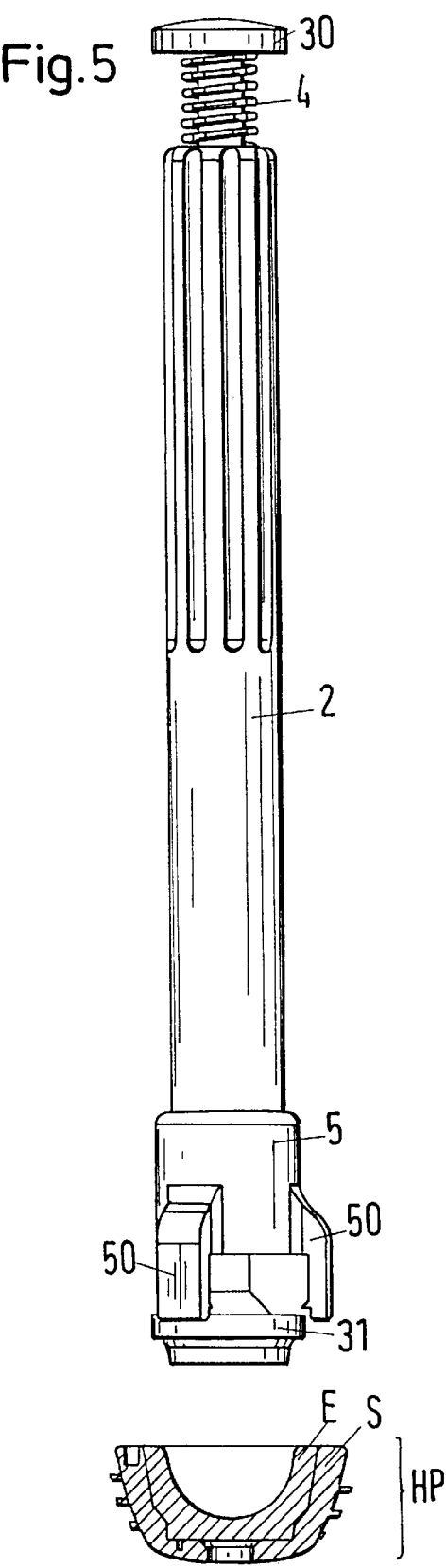

INSTRUMENT FOR THE INTRODUCTION OF AN INLAY OF AN IMPLANT INTO THE ASSOCIATED SHELL

The invention relates to an instrument for the introduction of an inlay of an implant, in particular of an artificial hip joint socket, into the associated shell of this implant in accordance with the preamble of the independent patent claim.

Some implants, in particular however artificial hip joint sockets, comprise a shell, for example of titanium, which is fastened to the hip bone, as well as an "inlay", which is inserted into the shell and which has a concave sliding surface for the shaft ball on its surface which faces away from th e shell. The inlay itself can be manufactured of plastic (e.g. polyethylene), of metal, of a ceramic or of a combination of such materials with other materials.

After the introduction of the inlay into the shell the inlay must be securely connected to the shell, but should also be releasable from the shell again when required (in order that it can be replaced when appropriate). The introduction of the inlay into the shell is done in the operating room. When a complete artificial hip joint socket is implanted, the shell of the artificial hip joint socket must first be fastened to the hip bone of the patient; afterwards the inlay can be introduced into the shell. In contrast, when the inlay is being replaced, no new shell is fastened to the hip bone; rather the old inlay is simply removed from the shell and then a new inlay is put in.

The connection of the inlay and the shell can be executed in different manners; one example of this is a snap connection between the inlay and the shell; in other words, the inlay snaps into the shell when introduced and is thereby firmly connected to it, but is releasable again when required. Other connections of the inlay and the shell are based on the fact that both the inner surface of the shell and the outer surface of the inlay are designed to converge conically and that the firm connection of the inlay and the shell occurs via the cone (i.e. via frictional forces). Combinations of these two connection kinds are also known. The introduction and securing of the inlay into the shell is done in the operating room under sterile conditions.

The object of the invention is to provide an instrument by means of which inlays of implants, in particular of artificial hip joint sockets, can be inserted in a simple and reliable manner into a corresponding shell and can be secured there. At the same time it should be possible to perform the insertion to a certain extent rapidly and independently of the respective position of the patient on the operating table. The inlay should be positioned with the help of the instrument in such a manner that a false insertion is practically impossible.

The object is satisfied in accordance with the invention by an instrument such as is characterized by the features of the independent patent claim. The instrument comprises a bar which has a holder apparatus at its distal end for holding the inlay firmly. Furthermore, it comprises an actuating member for releasing the inlay into the shell. The holder apparatus comprises at least three resilient lamella which point in the axial direction and are arranged in such a manner that their free ends point away from the bar. The lamella are shaped in such a manner that they form a snap connection together with the inlay when holding the inlay. In this manner the inlay is held securely between the lamella by the instrument and can be led to the shell without problem in any arbitrary position of the patient. With the help of the actuating member, the inlay can be released into the shell and fastened there so that the entire introduction can be performed simply, rapidly and reliably in the operating room and a false insertion is practically impossible.

In one exemplary embodiment of the instrument in accordance with the invention the lamella on its inner wall have a conical surface converging in the direction towards their free ends which form the snap connection in conjunction with a corresponding conical surface on the outer wall of the inlay. In this, the cone provided at the inner wall of the lamella has a diameter at the location of its greatest diameter which is smaller than or equal to the greatest outer diameter of the cone on the outer wall of the inlay. The lamella are spread apart when the inlay is inserted between the lamella and the cone provided on the inner surfaces of the lamella forms a firm seat with the cone on the outer surface of the inlay so that the inlay is held securely between the lamella. If at the location of its greatest diameter the diameter of the cone on the inner wall of the lamella is just equal to the greatest outer diameter of the inlay, then the inlay fits exactly between the lamella and is held there.

In a further development the cone angle of the cone on the inner wall of the respective lamella is greater than or equal to the cone angle on the outer wall of the inlay. Ideally the two cone angles should be of equal size so that the inlay is held firmly by the lamella practically over its entire conical surface.

In a further exemplary embodiment, a projection protruding inwardly in the radial direction is provided in each case at the proximal end of the conically converging surfaces on the inner wall of the lamella, that is, where the cone provided on the inner wall of the lamella has its greatest diameter. This projection forms an abutment for the inlay; the inlay is thus pressed against the abutment between the lamella so that it is always held in a precisely defined (and usually centered) position.

A further exemplary embodiment is distinguished by the fact that the distal end of the conically converging surface of the respective lamella is provided with a bevel edge. This bevel edge facilitates the guiding in of the inlay between the lamella between which the inlay is then held. Furthermore, the snap connection between the lamella and the inlay results from the guiding in of the inlay past the projection formed by the bevel edge and the following conical surface.

In a further exemplary embodiment the bar is substantially formed as a hollow cylinder. The actuating member for releasing the inlay has a thrust rod with a plunger fastened to its distal end, with the thrust rod being guided in the hollow cylindrical bar and movable in the longitudinal direction against the force of a restoring spring. (The restoring spring is not obligatory, but it increases the user friendliness). When the thrust rod is actuated the plunger dips in between the lamella and pushes out the inlay which is held between the lamella. Afterwards the thrust rod together with the plunger is moved back to its rest position by means of the restoring spring. This exemplary embodiment is constructionally simple, is simple in its manipulation and is furthermore also simple to assemble and disassemble. This in turn is advantageous in view of the fact that the instruments must be sterilized regularly.

In order to simplify the assembly and disassembly of the instrument even further, and/or also to simplify the sterilization, the holder apparatus can comprise a separate holder head which is releasably connected to the bar and on which the lamella are provided. In this exemplary embodiment the instrument can be practically decomposed into its individual parts and can thereby also be sterilized in a simple manner. In addition the manufacture of the individual parts of such an instrument is simplified. The holder head can for example be screwed tightly by means of an inner thread onto an outer thread on the bar.

Further advantageous aspects of the invention result from the following description with the help of the drawing. Shown are:

FIG. 1 an exemplary embodiment of the instrument in accordance with the invention in its rest position and without an inlay for the shell of a hip joint socket, FIG. 2 the exemplary embodiment of FIG. 1, but with an inlay for a likewise illustrated shell of a hip join t socket, FIG. 3 the detail III of FIG. 2, FIG. 4 the exemplary embodiment of FIG. 1 during the insertion of the inlay into th e shell of a hip joint socket, and FIG. 5 the instrument in the position immediately after the insertion and securing of the inlay in the shell of a hip joint socket.

In the exemplary embodiment illustrated in FIG. 1 of the instrument 1 in accordance with the invention for the introduction of an inlay E of an implant, in particular of a hip joint socket HP (FIG. 2), into the associated shell S (FIG. 2) of the implant one recognises an elongate hollow cylindrical bar 2 in which a thrust rod 3 is guided. The thrust rod 3 is movable against the force of a restoring spring 4 in the hollow cylindrical bar 2 in that the operating person (e.g. the surgeon or the orthopaedist) presses on the proximally arranged button 30. At its distal end the thrust rod 3 has a plunger 31 which e.g. is connected via a screw connection (FIG. 4) to the thrust rod 3 (and can thus be released and simply sterilised). Furthermore, a holder apparatus is provided at the distal end of the instrument 1 in the form of a separate holder head 5 which is connected to the bar 2 e.g. via a screw connection (FIG. 4) (which further facilitates the sterilisation of the individual parts). At its distal end the holder head 5 has three resilient lamella or fingers 50 (displaced in each case by 120° in the peripheral direction), the free end of each lamella points away from the bar 2 in the axial direction. Oh their inner wall the lamella 50 have a conical surface 500 converging in the direction towards their free end (that is, in the direction towards the distal end). Furthermore, the lamella 50 have a projection 501 protruding inwardly in the radial direction at the proximal end of this conically converging surface 500, that is, where the cone has its greatest diameter.

In FIG. 2 one recognizes the exemplary embodiment of the instrument in accordance with the invention of FIG. 1, with, however, the inlay E of the hip joint socket HP being held between the lamella 50. This inlay E is inserted into the shell S with the help of the instrument 1. In practice, one can imagine that the shell S is already anchored in the hip bone of the patient, with the patient lying in a position on the operating table which is favourable for the surgeon or orthopaedist. For the description of the instrument in accordance with the invention and its method of operation, however, only the shell S is illustrated here for the sake of simplicity in each case (and an illustration of e.g. the hip bone is dispensed with).

One recognizes further in FIG. 2 that the thrust rod 3 is illustrated to be already moved out of its rest position by a certain distance, since the plunger 31 has already partially engaged between the lamella 50 (one also recognizes this in the slightly compressed restoring spring 4), however not yet to such an extent that it pushes the inlay E which is held between the lamella 50 out into the shell S.

FIG. 3 shows the detail III of FIG. 2 in an enlarged view. In FIG. 3 one recognizes particularly well the manner in which the inlay E is held between the lamella, with only a section of one lamella 50 and only one section of the inlay E being illustrated for the sake of simplicity. One recognizes that the inlay E has a conical surface K on its outer wall, which forms a firm seat together with the conical surface 500 on the inner wall of the lamella 50. The distal end of the conical surface 500 is provided with a bevel-edge 502 so that when the inlay is being introduced between the lamella 50 the inlay can be introduced while being guided in a simple manner between the lamella 50, and when introduced beyond the projection formed by the bevel-edge 502 and the conical surface 500 a snap connection is formed. The resiliently executed lamella 50 recede resiliently during the introduction of the inlay E between the lamella since the diameter of the cone on the inner wall of the lamella 50 at the distal end is in any case less than the diameter of the cone at the proximal end on the outer wall of the inlay E (it is namely the greatest there). At the proximal end (that is, where the diameter is the greatest) the diameter of the cone on the inner wall of the lamella 50 is likewise less than or just equal to the greatest outer diameter of the cone on the outer wall of the inlay E. The cone angle $\alpha$ (FIG. 1) of the cone on the inner wall of the lamella 50 is (somewhat) greater than or exactly equal to the cone angle $\beta$ (FIG. 3) of the cone on the outer wall of the inlay E.

In FIG. 4 the instrument 1 is illustrated in a longitudinal section (practically, rotated by 180° about the longitudinal axis), with an inlay E which is held firmly by the instrument 1 between the lamella 50 just being inserted into the shell S of a hip joint socket HP and being secured there in the illustration of FIG. 4. One recognises that the shell S has threaded portions G on its outer wall (see also FIG. 2), with the help of which it is possible to fasten the shell S in the (non-illustrated) hip bone. In addition, however, the shell S also has a central bore B through which a suitable anchoring means—e.g. a (non-illustrated) screw—is passed, with this screw being screwed into the hip bone and the shell S being anchored thereby.

For the introduction of the inlay E into the already anchored shell S the instrument 1 is now placed with the flat front ends of the three lamella 50 onto the upper rim of the shell S. Then the surgeon or orthopaedist pushes on the button 30 at the proximal end of the thrust rod 3, through which the restoring spring 4 is compressed and the plunger 31 pushes the inlay E which is held between the lamella 50 into the shell S. In the exemplary embodiment shown here the surgeon or orthopaedist will press on the button 30 on the proximal end of the thrust rod 3 until the inlay E has been pushed completely into the shell S by the thrust rod 3 and the plunger 31 and—in this exemplary embodiment—a snap connection which is formed by the other two conical surfaces, at the lower end of the shell S and on the inlay E, has snapped into place. Obviously, however, a snap connection of this kind need not be provided at the lower end of the shell S and the inlay E for the firm seating of the inlay E in the shell S. A cone connection typically provided for cases of this kind is absolutely sufficient for a firm seating of the inlay E in the shell S.

Finally, FIG. 5 shows an inlay E which has been completely fitted into the shell S, with the instrument which had been placed on the upper rim of the shell S during the introduction having been lifted off again from the hip joint socket HP, but with the button 30 on the proximal end of the thrust rod 3 still being illustrated in the depressed position. One recognizes this on the one hand by the still compressed restoring spring 4 and, on the other hand, by the plunger 31 at the distal end of the thrust rod 3 which is still completely dipped in between the lamella 50 (practically up to the free end of the lamella.

As a result of the use of the instrument in the operating room, the individual parts of the instrument must be sterilizable. Whereas the thrust rod 3 with the head 30 can be manufactured of a non-rusting metal, e.g. of a stainless steel, the hollow cylindrical bar 2 can be manufactured for example of polyoxymethylene (POM-C). The holder head 5 with the three flexible lamella or fingers (naturally more than three lamella can also be provided) can for example be manufactured of polyetherimide. Finally, the plunger 31 can likewise be manufactured of a sterilizable plastic.

The shell S can for example be manufactured of titanium, whereas the inlay E can be manufactured of polyethylene (PE, ISO 5834-2), of a ceramic on an aluminium oxide base (e.g. a ceramic ISO 6474-A which can be obtained under the trade mark CERASUL® of the applicant) or of a metallic cobalt-chromium-molybdenum alloy (e.g. a metallic alloy ISO 5832-12 which can be obtained under the trade mark METASUL® of the applicant).

We claim:

1. An instrument for the introduction of an inlay into an artificial hip joint socket shell, comprising:

an elongated bar having a longitudinal axis, a proximal end, and a distal end;

a holder mounted on the distal end of the bar for holding the inlay; and an actuating member associated with the bar for releasing the inlay from the holder and into the shell;

wherein the holder further comprises at least three resilient lamellas which are integrally attached to the holder and extend away from the holder and the distal end of the bar in a direction substantially parallel to the longitudinal axis of the bar, each lamella having a distal free end with an inner surface which is shaped and configured so that the lamellas can grip and hold the inlay.

2. The instrument of claim 1, wherein each lamella has an inner surface at the distal free end which comprises a portion of a conical surface having a first cone angle, the conical surfaces of the lamellas together defining a portion of a cone which converges in a direction towards the free end of the lamellas and forms a firm seat together with a corresponding conical surface having a second cone angle on an outer surface of the inlay, with the cone defined by the inner surfaces of the lamellas having a greatest diameter which is smaller than or equal to a greatest outer diameter of the conical surface of the inlay.

3. The instrument of claim 2, wherein the first cone angle is greater than or equal to the second cone angle.

4. The instrument of claim 2, wherein the inner surface of each lamella comprises a protrusion projecting inwardly in a radial direction, the protrusions on the lamellas forming an abutment for the inlay.

5. The instrument of claim 2, wherein the inner surface of each lamella is provided with a bevel for ease in mounting the inlay.

6. The instrument of claim 1, wherein the bar comprises a substantially hollow cylinder, and wherein the actuating member comprises a thrust rod with a plunger connected to a distal end, the thrust rod being guided within the bar and being movable along the longitudinal axis of the bar against a force of a restoring spring, whereby the plunger engages between the lamellas when the thrust rod is actuated from a rest position and ejects an inlay being held between the lamellas, and whereby the thrust rod and plunger are subsequently moved back to the rest position by means of the restoring spring.

7. The instrument of claim 1, wherein the holder comprises a separate holder head which is releasably connectable to the bar.

* * * * *